US008696555B2

(12) United States Patent
Mizuno (10) Patent No.: US 8,696,555 B2
(45) Date of Patent: Apr. 15, 2014

(54) LIGHT SOURCE DEVICE AND ENDOSCOPE DEVICE

(75) Inventor: Kyosuke Mizuno, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 943 days.

(21) Appl. No.: 12/111,242

(22) Filed: Apr. 29, 2008

(65) Prior Publication Data

US 2008/0278963 A1 Nov. 13, 2008

(30) Foreign Application Priority Data

May 10, 2007 (JP) ................................ 2007-126081

(51) Int. Cl.
*A61B 1/06* (2006.01)

(52) U.S. Cl.
USPC ........................... 600/180; 600/181; 600/178

(58) Field of Classification Search
USPC .......... 600/181, 180, 160, 109, 178; 362/552, 362/574, 572
See application file for complete search history.

(56) References Cited

U.S. PATENT DOCUMENTS

| 4,233,650 | A | * | 11/1980 | Hagner et al. ................ 362/552 |
| 4,425,599 | A | * | 1/1984 | Rieder et al. .................. 362/552 |
| 4,562,477 | A | * | 12/1985 | Ogasawara et al. ............ 348/364 |
| 4,710,807 | A | | 12/1987 | Chikama |
| 4,998,129 | A | | 3/1991 | Watanabe et al. |
| 5,868,666 | A | * | 2/1999 | Okada et al. .................... 600/118 |
| 6,080,104 | A | * | 6/2000 | Ozawa et al. ................... 600/180 |
| 6,231,504 | B1 | * | 5/2001 | Honda et al. ................... 600/180 |
| 6,261,228 | B1 | * | 7/2001 | Honda et al. ................... 600/180 |
| 6,320,331 | B1 | * | 11/2001 | Iida et al. ....................... 315/293 |
| 6,334,845 | B1 | * | 1/2002 | Higuchi et al. ................ 600/181 |
| 6,367,958 | B1 | * | 4/2002 | Jones ............................. 362/552 |
| 6,422,996 | B2 | * | 7/2002 | Higuchi et al. ................ 600/181 |
| 6,524,236 | B2 | * | 2/2003 | Honda et al. ................... 600/180 |
| 6,629,925 | B2 | * | 10/2003 | Kurosawa et al. ............. 600/180 |
| 6,724,418 | B1 | * | 4/2004 | Takahashi ....................... 348/65 |

(Continued)

FOREIGN PATENT DOCUMENTS

| JP | 61-9628 | 1/1986 |
| JP | 62-161338 A | 7/1987 |

(Continued)

OTHER PUBLICATIONS

Japanese Office Action dated Oct. 30, 2012 in corresponding Japanese Patent Application No. 2007-126081.

*Primary Examiner* — Philip R Smith
*Assistant Examiner* — William Chou
(74) *Attorney, Agent, or Firm* — Scully, Scott, Murphy & Presser, P.C.

(57) ABSTRACT

A light source device includes a light source, a diaphragm blade for adjusting light quantity of illumination light supplied from the light source, a diaphragm driving part for driving the diaphragm blade to perform opening/closing operation, and a diaphragm control circuit part for setting diaphragm drive instruction voltage to be supplied to the diaphragm driving part and control an opening/closing amount of the diaphragm blade. In the diaphragm control circuit part, a fully-opened voltage and a fully-closed voltage at the time the diaphragm blade is fixed at a fully-opened position and a fully-closed position are read, based on the voltages, adjustment data for adjusting the diaphragm drive instruction voltage and the opening/closing positions of the diaphragm blade is set, and based on the adjustment data, a control range of the diaphragm drive instruction voltage is regulated.

8 Claims, 5 Drawing Sheets

(56) References Cited

U.S. PATENT DOCUMENTS

| | | | |
|---|---|---|---|
| 6,829,003 B2 * | 12/2004 | Takami | 348/76 |
| 6,932,763 B2 * | 8/2005 | Ayame | 600/181 |
| 6,974,240 B2 * | 12/2005 | Takahashi | 362/574 |
| 6,980,227 B2 * | 12/2005 | Iida et al. | 348/69 |
| 7,029,437 B2 * | 4/2006 | Kobayashi | 600/180 |
| 7,070,560 B2 * | 7/2006 | Takahashi | 600/178 |
| 7,232,410 B2 * | 6/2007 | Takahashi | 600/180 |
| 7,306,533 B2 * | 12/2007 | Ito | 475/5 |
| 7,419,450 B2 * | 9/2008 | Ito | 475/5 |
| 7,448,995 B2 * | 11/2008 | Wiklof et al. | 600/173 |
| 7,573,499 B2 * | 8/2009 | Doguchi et al. | 348/65 |
| 7,623,150 B2 * | 11/2009 | Kobayashi | 348/45 |
| 7,651,255 B2 * | 1/2010 | Ito | 362/574 |
| 7,828,726 B2 * | 11/2010 | Negishi | 600/178 |
| 7,853,106 B2 * | 12/2010 | Takahashi et al. | 385/117 |
| 2001/0002849 A1 | 6/2001 | Arai | |
| 2003/0060683 A1 * | 3/2003 | Abe et al. | 600/180 |
| 2004/0122291 A1 * | 6/2004 | Takahashi | 600/180 |
| 2005/0010083 A1 * | 1/2005 | Iriyama | 600/180 |
| 2005/0143627 A1 * | 6/2005 | Cline et al. | 600/181 |
| 2006/0088303 A1 * | 4/2006 | Ito | 396/17 |
| 2007/0010712 A1 * | 1/2007 | Negishi | 600/178 |

FOREIGN PATENT DOCUMENTS

| | | |
|---|---|---|
| JP | 03-092810 A | 4/1991 |
| JP | 11-242254 A | 9/1991 |
| JP | 2000-241718 | 9/2000 |
| JP | 2003-061905 | 3/2003 |
| JP | 2003-126032 A | 5/2003 |
| JP | 2005-176398 A | 6/2005 |

* cited by examiner

LIGHT SOURCE DEVICE AND ENDOSCOPE DEVICE

This application claims benefit of Japanese Application No. 2007-126081 filed on May 10, 2007, the contents of which are incorporated by this reference.

BACKGROUND OF THE INVENTION

1. Field of the Invention

The present invention relates to a light source device and an endoscope device that automatically adjust light quantity of illumination light using a diaphragm member.

2. Description of the Related Art

Generally, light source devices used in endoscope devices or the like have a diaphragm unit that adjusts light quantity of illumination light supplied from a light source to irradiate a subject so that luminance of light forming an image on a photo acceptance element such as a charge coupled device (CCD) is to be substantially constant.

As means for adjusting the light quantity of the illumination light, for example, Japanese Unexamined Patent Application Publication No. 2000-241718 discloses a light source device that has a diaphragm member on an optical path of illumination light emitted from a light source, and an opening/closing amount of the diaphragm member is controlled so that the luminance becomes substantially constant. That is, the light source device disclosed in the document, in controlling the opening/closing amount of the diaphragm member, compares a light quantity adjustment signal generated by a light quantity adjustment signal generation circuit based on a luminance signal received by a CCD with reference voltage of brightness appropriate for observation. Then, the opening/closing amount of the diaphragm member is adjusted based on the error signal, and the light quantity is automatically adjusted so that the level of the light quantity adjustment signal corresponds to the reference voltage.

SUMMARY OF THE INVENTION

In view of the above, it is an object of the present invention to provide a light source device and an endoscope device capable of obtaining stable luminance without manual adjustment operation, and even if an error is generated between a control voltage width and opening/closing positions of a diaphragm blade due to foreign elements such as vibration in transportation after assembly, capable of adjusting the error appropriately. Further, the light source device and the endoscope device can automatically perform the adjustment on changes across the ages, and reduce maintenance costs.

According to an aspect of the present invention, a light source device includes a light source; a diaphragm member for adjusting light quantity of illumination light supplied from the light source; a diaphragm driving part for driving the diaphragm member to perform opening operation or closing operation; an opening/closing control part for setting electric energy to be supplied to the diaphragm driving part and control an opening/closing amount of the diaphragm member; and a control range setting part for detecting fixed position information at the time the diaphragm member is fixed at a predetermined position, setting adjustment data for adjusting a drive signal outputted from the opening/closing control part and opening/closing positions of the diaphragm member based on the fixed position information, and regulating a control range of the opening/closing control part based on the adjustment data.

According to the present invention, the fixed position information when the diaphragm member is fixed at the predetermined position is detected, and based on the fixed position information, the control range of the opening/closing control part is regulated by adjusting the drive signal outputted from the opening/closing control part for setting the electric energy to be supplied to the diaphragm driving part that drives the diaphragm member to perform the opening/closing operation and opening/closing positions of the diaphragm member. Accordingly, the error between the voltage control range of the diaphragm driving part and the opening/closing positions of the diaphragm member is automatically adjusted. Thus, manual adjustment operation is not required and high adjustment accuracy can be obtained. Further, since the error between the voltage control range of the diaphragm driving part and the opening/closing positions of the diaphragm blade is automatically adjusted, an error generated due to changes across the ages can also be automatically adjusted and it is possible to realize the maintenance costs reduction.

DETAILED DESCRIPTION OF THE PREFERRED EMBODIMENT

An embodiment of the present invention is described with reference to the attached drawings. In the present embodiment, a light source device is provided in an endoscope device. However, in addition to the endoscope device, the light source device may be applied to other devices that require a light source.

Figure 1:
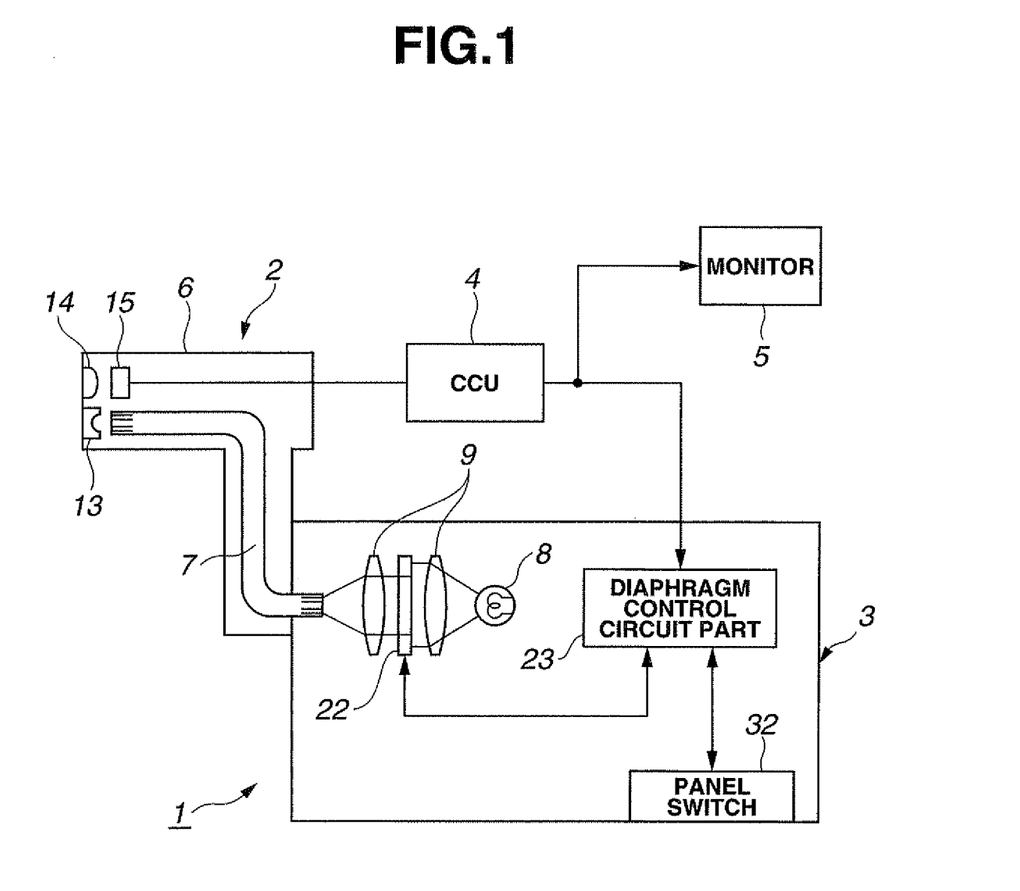
FIG. 1 is an overall view illustrating a configuration of an endoscope device.

As shown in FIG. 1, an endoscope device 1 includes an electronic endoscope 2 to be inserted into a body cavity, a light source device 3 that supplies illumination light to the electronic endoscope 2, a camera control unit (CCU) 4 that performs signal processing to image pickup device 15 such as a CCD provided in the electronic endoscope 2, and a monitor 5 that displays an endoscopic image using a video signal outputted from the CCU 4. The CCU 4 generates a light adjustment signal corresponding to brightness of an image captured by, for example, performing integration on a luminance signal for one frame period, and outputs the light adjustment signal to the light source device 3.

The electronic endoscope 2 includes an elongated insertion portion 6 to be inserted into a body cavity or the like. A light guide 7 that transmits illumination light is inserted through the insertion portion 6. A hack end face of the light guide 7 is fixed and connected to the light source device 3. A illumination lens 13 is provided on an distal end face of the insertion portion 6 and in front of an output face of the light guide 7. An objective lens 14 is provided on the distal end face of the insertion portion 6, and an image pickup face of the image pickup device 15 is provided at an image forming position of the objective lens 14.

Illumination light emitted from the output face of the light guide 7 of the electronic endoscope 2 irradiates an object, and the reflected light is taken into the electronic endoscope 2. The taken reflected light forms an image on the image pickup face of the image pickup device 15 through the objective lens 14, and a photoelectric-converted electrical signal is transmitted to the CCU 4. The CCU 4 performs signal processing on the electronic signal transmitted from the image pickup device 15, and generates the above-described video signal and light adjustment signal.

The light source device 3 includes a light source lamp 8 that functions as a light source for supplying illumination light to the light guide 7, condensing lenses 9 that condense the illumination light, a diaphragm unit 22 that is positioned between the condensing lenses 9 and has a diaphragm blade 21 (see FIG. 2) that functions as a diaphragm member for adjusting the illumination light supplied from the light source lamp 8 to appropriate light quantity, a control circuit part 23 that drives the diaphragm blade 21, and a panel switch 32.

The control circuit part 23 automatically controls (automatically adjusts) the light quantity of the illumination light supplied from the light source device 3 to the light guide 7 based on the light quantity adjustment light outputted from the CCU 4, and always keeps an endoscopic image displayed on the monitor 5 at constant brightness.

The panel switch 32 is a generic name of each operation switch provided on an operation panel such as a luminance setting switch for setting brightness of endoscopic images displayed on the monitor 5 at any brightness, a changeover switch for selecting whether to automatically or manually set the brightness, an adjustment operation switch for operation of manual adjustment of characteristics of the diaphragm blade 21, and the like, and each operation switch is connected to the diaphragm control circuit part 23.

Figure 2:
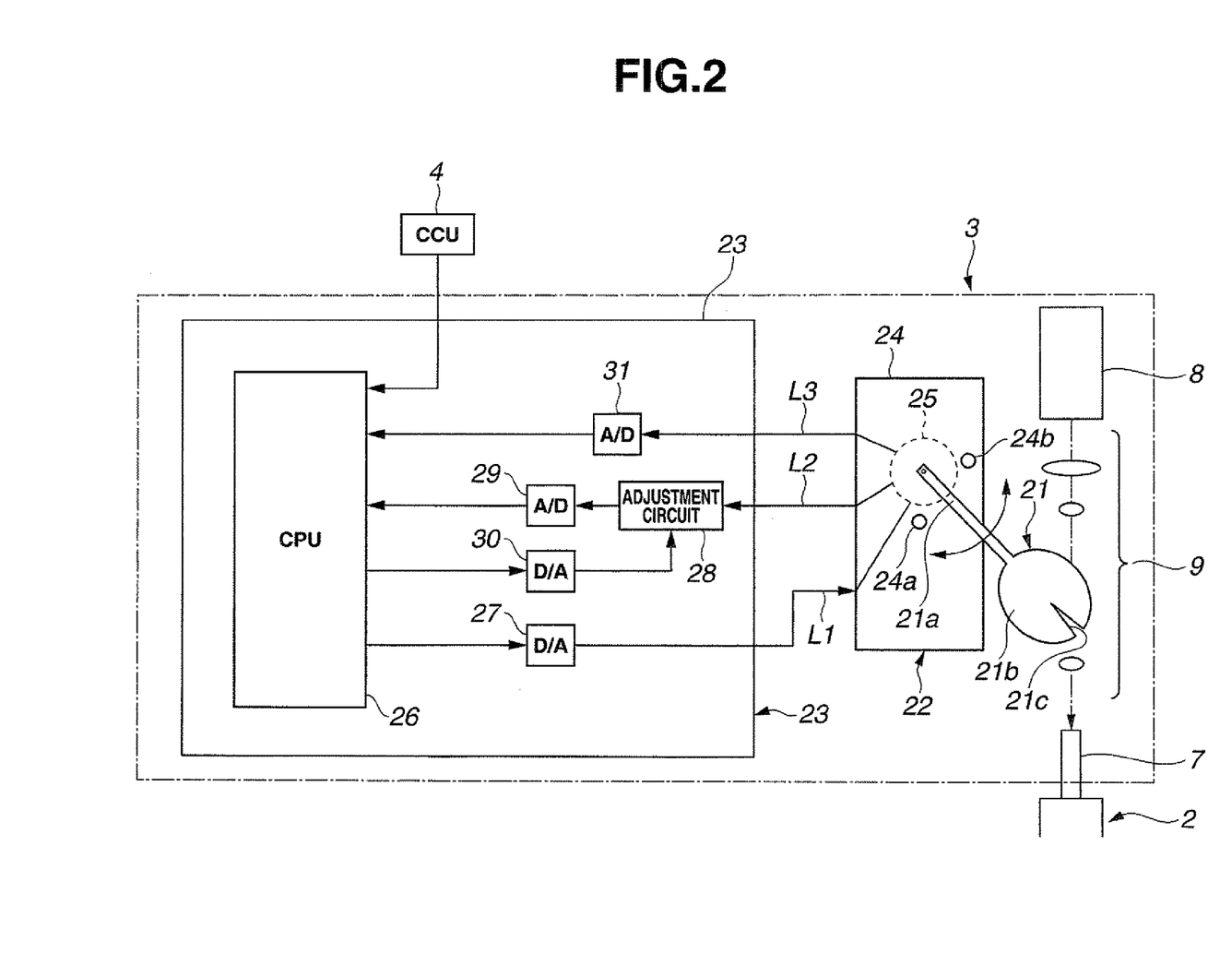
FIG. 2 is a configuration diagram of a diaphragm control circuit part and a diaphragm unit.

As shown in FIG. 2, the diaphragm unit 22 includes a base plate 24 and a diaphragm driving part 25 that is fixed to the base plate 24 such as a DC motor, a rotary actuator, or the like. The diaphragm driving part 25 has a rotary shaft, and a magnet is fixed to the rotary shaft. Around the magnet, a drive coil, a braking coil that generates induced electromotive force in rotation of the diaphragm blade 21 and puts brake on the rotation operation of the diaphragm blade 21, and a potentiometer that detects a rotation angle of the diaphragm blade 21. The potentiometer may be a hall element or a rotary encoder.

To the rotary shaft of the electric driving part 25, a base part of an arm 21*a* of the diaphragm blade 21 is rotatably attached to perform open/close operation. At a top of the arm 21*a* of the diaphragm blade 21, a substantially disc-shaped shielding part 21*b* is formed. In the shielding part 21*b*, a substantially fan-shaped notched part 21*c* is formed. The notched part 21*c* faces on an optical path of illumination light, and at the notched part 21*c*, light quantity of the illumination light passing through the optical path is adjusted by the open/close operation of the diaphragm blade 21. On the base plate 24, stopper pins 24*a* and 24*b* that regulate a rotation range of the diaphragm blade 21 are provided in a protruding condition. The stopper pins 24*a* and 24*b* regulate a maximum rotation range of the diaphragm blade 21. At a position where the arm 21*a* of the diaphragm blade 21 is latched by the stopper pin 24*a*, the optical path is fully opened, and at a position where the arm 21*a* is latched by the stopper pin 24*b*, the optical path is fully closed.

A drive signal line L1 is connected to an input end of the drive coil, a braking signal line L2 is appropriately connected to an output end of the braking coil via an amplifier, and a diaphragm position signal line L3 is connected to an output end of the potentiometer. Each of the signal lines L1, L2, and L3 is connected to the diaphragm control circuit part 23.

The diaphragm control circuit part 23 includes a CPU (central processing unit) 26, and the drive signal line L1 is connected to an output side of the CPU 26 via a D/A (digital/analogue) conversion circuit 27. The braking signal line L2 is connected to an input side of the CPU 26 via an adjustment circuit 28 and an A/D (analogue/digital) conversion circuit 29. The output side of the CPU 26 is negative feedback-connected to the adjustment circuit 28 via a D/A conversion circuit 30. The adjustment circuit 28 adjusts an output value of the induced electromotive force outputted from the braking coil to be inputted into the CPU 26 to 0 [V] in a state that the diaphragm blade 21 is fixed at any opening position. The diaphragm position signal line L3 is connected to the input side of the CPU 26 via an A/D conversion circuit 31.

The CPU 26 compares a light adjustment signal outputted from the CCU 4 to a reference value corresponding to brightness that has been set in advance according to a control program that has been stored in advance, and sets a diaphragm drive instruction voltage signal as electric energy. Then, the CPU 26 D/A-converts the diaphragm drive instruction voltage signal in the D/A conversion circuit 27, and outputs the converted signal to the diaphragm driving part 25 via the drive signal line L1. In response to the output, the drive coil is exited, and by a correlation between the excitation of the drive coil and the magnetic field of the magnet fixed on the rotary shaft, the diaphragm blade 21 rotates. Accordingly, the CPU 26 has a function as an opening/closing control part for controlling an opening/closing amount of the diaphragm blade 21.

In response to the rotation of the diaphragm blade 21, the magnetic field of the magnet is changed and by the change of the magnetic field, induced electromotive force is generated in the braking coil. The induced electromotive force is substantially proportional to the rotation speed of the diaphragm blade 21, and the induced electromotive force increases as the rotation speed of the diaphragm blade 21 increases. By the induced electromotive force, the rotation speed of the diaphragm blade 21 is suppressed.

The rotation operation of the diaphragm blade 21 is detected by the potentiometer, and the detected signal (voltage) is appropriately amplified, A/D-converted by the A/D conversion circuit 30 via the diaphragm position signal line L3, and inputted into the CPU 26. If the voltage detected by the potentiometer and the diaphragm drive instruction voltage becomes a same volume, the rotation of the diaphragm blade 21 is stopped.

Figure 3:
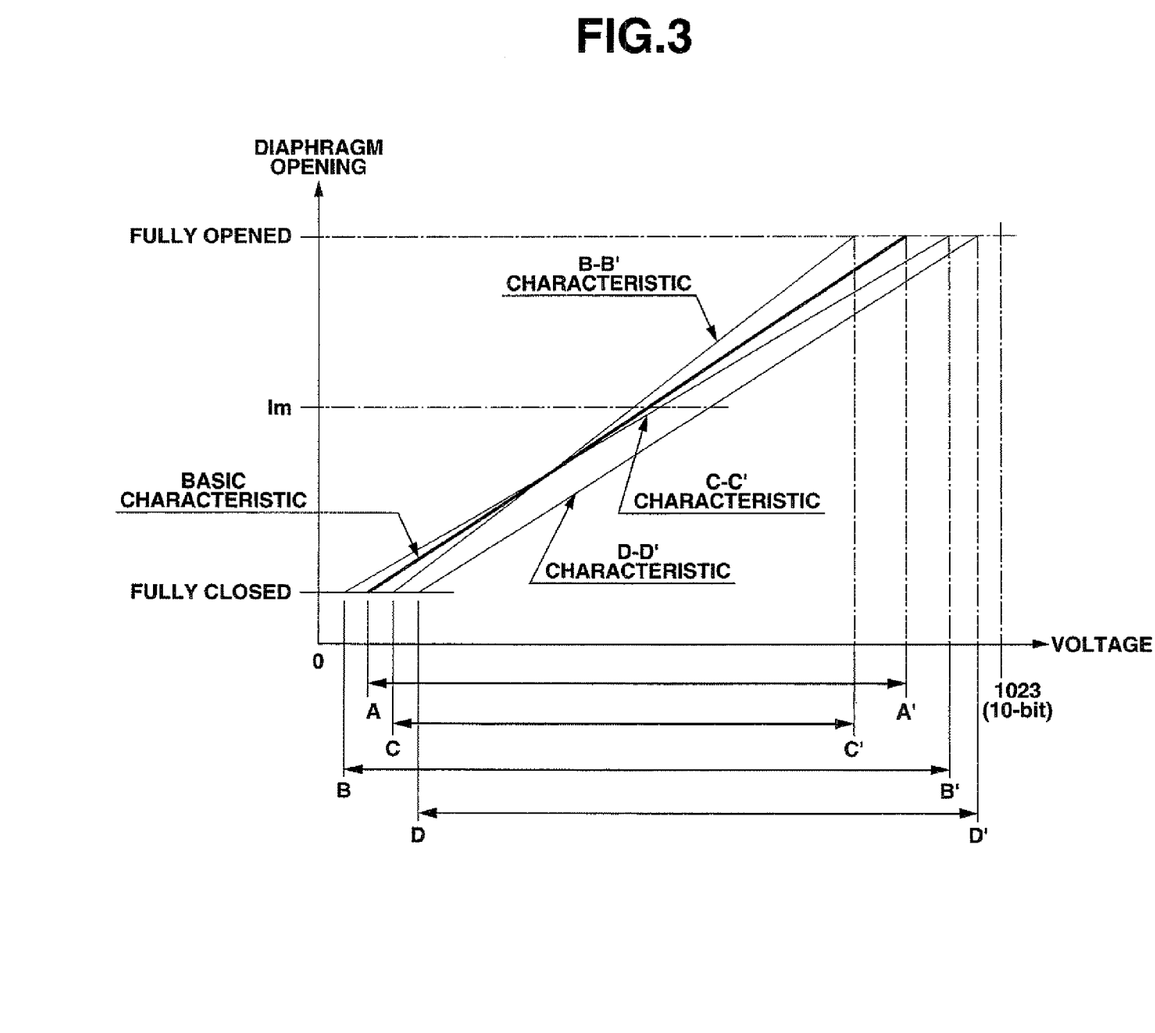
FIG. 3 is a characteristic view illustrating a relationship between voltages detected by a potentiometer and opening degrees of a diaphragm blade.

Meanwhile, since the diaphragm unit 22 composed of the diaphragm blade 21, the diaphragm driving part 25, and the like is a mechanical component, due to a balance error in assembly or changes across the ages, errors may be generated between the voltage control width outputted from the diaphragm driving part 25 and the opening/closing positions of the diaphragm blade 21 whose opening/closing amount is controlled by the voltage. That is, as shown in FIG. 3, if voltage (expressed as 10 bit in the drawing) detected by the potentiometer is shown along the horizontal axis and the diaphragm opening is shown along the vertical axis, at a position the arm 21*a* of the diaphragm blade 21 is latched by the stopper pin 24*a*, the diaphragm blade 21 is fully opened, and at a position where the arm 21*a* is latched by the stopper pin 24*b*, the diaphragm blade 21 is fully closed. The fully-opened position and the fully-closed position are uniquely set. Accordingly, a range from the position where the diaphragm blade 21 is latched by the stopper pin 24*a* to the position where the device 21 is latched by the stopper pin 24*b* is a maximum rotation range. A voltage control range of the diaphragm driving part 25 that rotates the diaphragm blade 21 is set to be wider than that of the diaphragm blade 21.

Accordingly, if the voltage outputted the from diaphragm driving part 25 is 0 [V], the diaphragm blade 21 has already been fully closed. Then, at the time diaphragm blade 21 is fully-opened, the voltage is set to a value lower than a maximum voltage (1023 in 10 bit expression), for example, 900 or less in 10 bit expression. According to a basic characteristic (design characteristic) shown by a thick line in the drawing, a control voltage width A-A' (for example, in 10 bit expression, A=70, A'=800) is set as the maximum rotation range. However, as shown in a B-B' characteristic, a C-C' characteristic, and a D-D' characteristic, between the voltage widths from the fully-opened position to the fully-closed position detected by the potentiometer and the maximum rotation range of the diaphragm blade 21, errors are generated due to effects such as an error in assembly of the diaphragm unit 22, or changes across the ages. In the present embodiment, the errors are automatically adjusted at the time the light source device 3 is actuated.

Figure 4:
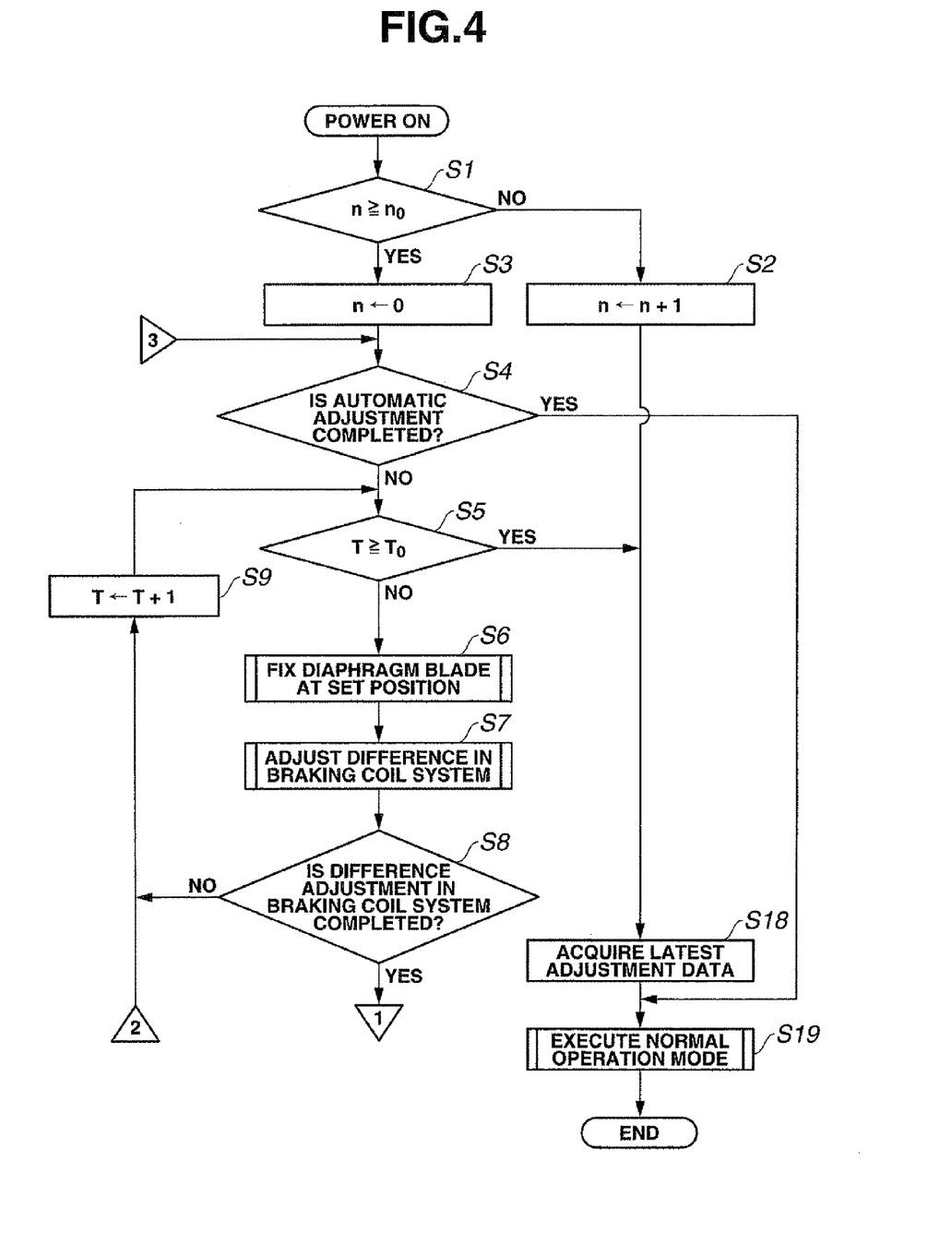
FIG. 4 is a flowchart (1) illustrating a start-up processing routine.
Figure 5:
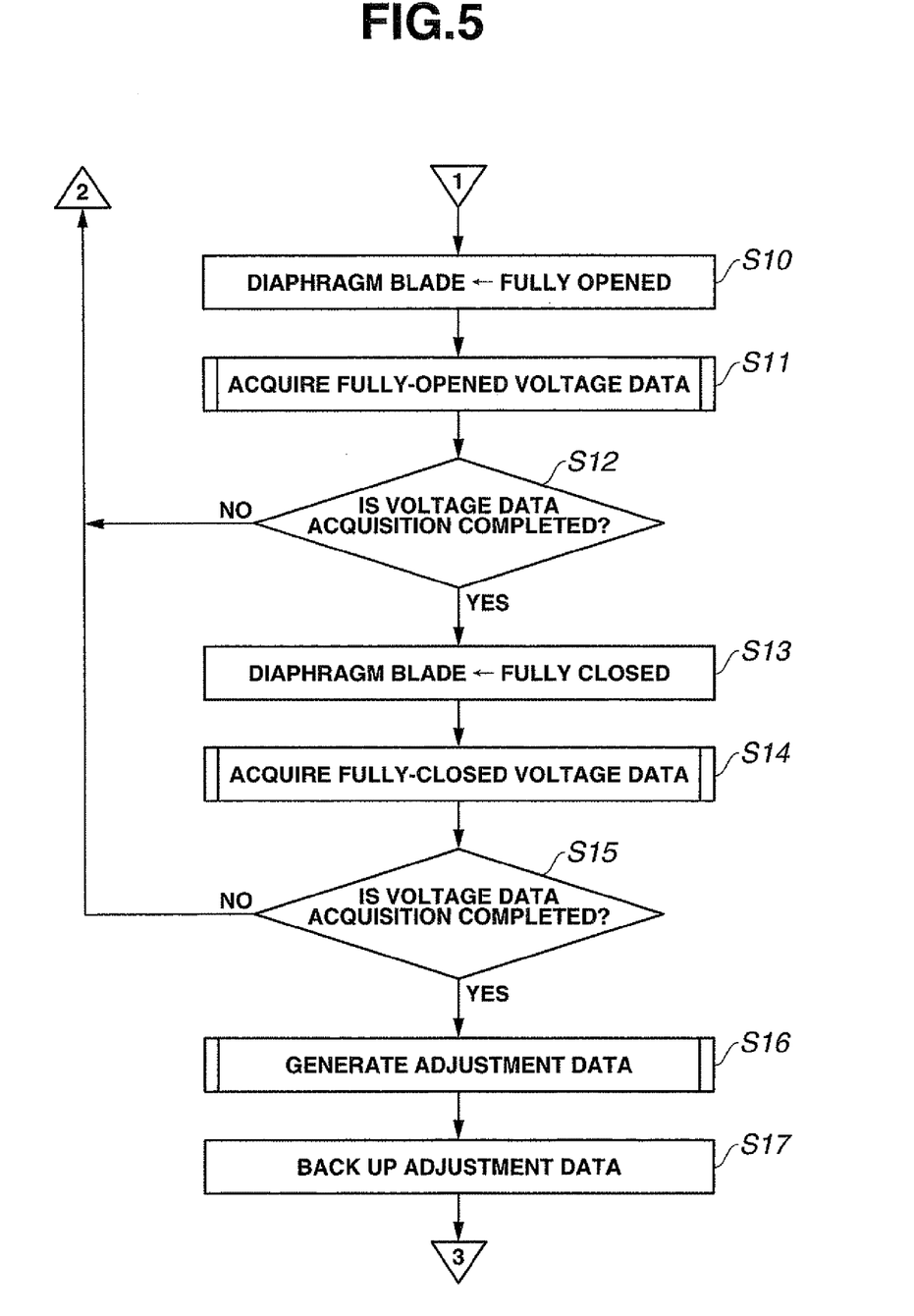
FIG. 5 is a flowchart (2) illustrating a start-up processing routine.

The automatic adjustment of the errors generated between the voltage width detected by the potentiometer and the maximum rotation range of the diaphragm blade 21 performed by the CPU 26 provided in the control circuit part 23 of the light source device 3 is, specifically, performed according to a start-up routine shown in FIGS. 4 and 5.

In the routine, in response to power supply to the light source device 3 by turning on the power switch of the light source device 3, first, in step S1, the CPU 26 checks whether an integrated value of the number of power supplies n reaches a set number of times no or not. The set number of times no is used to set a frequency of the automatic adjustment and can be set to any value. For example, if $n_O=1$ the CPU 26 detects an ON-signal of the power switch and performs the automatic adjustment processing every time. If $n_O=10$, the CPU 26 performs the automatic adjustment processing every 10 times of power supply. The automatic adjustment frequency may be set according to a total operating time of the light source device 3 in place of the number of times of power supply. That is, if the total operating time of the light source device 3 from completion of previous automatic adjustment processing reaches set time, a next automatic adjustment processing is performed at power supply after the reach of the total operating time to the set time.

If $n<n_O$, it is not necessary to perform the automatic adjustment processing, and the processing proceeds to step S2. In step S2, the integrated value of the number of power supplies n is incremented (n←n+1), and the processing directly proceeds to step S18. On the other hand, if $n≥n_O$, the processing proceeds to step S3 to perform the automatic adjustment processing. In such a case, in response to power supply, if an adjustment operation switch that functions as adjustment instruction device is manually turned on, the mode is switched to a manual mode. Then, if an on-signal that is an instruction signal at the time is inputted, the program is executed from step S3.

In step S3, the integrated value of the number of power supplies n is cleared (n←0), the processing proceeds to step S4. In step S4, the CPU 26 checks whether the automatic adjustment is completed or not, and if the automatic adjustment is not completed, the processing proceeds to step S5. If start-up adjustment processing performed after step S5 is completed, the processing directly proceeds to step S19.

If it is determined that the automatic adjustment is not completed and the processing proceeds to step S5, the CPU 26 checks whether waiting time count value T after the power supply has reached a set count value $T_0$ (for example, a value corresponding to 5 seconds) or not. If it is determined that the waiting time of $T<T_0$ has not reached the set time, the processing proceeds to step S6. If the waiting time of $T≥T_0$ has reached the set time, the processing directly proceeds to step S18. If the automatic adjustment is executed after power is supplied to the light source device 3, it is not possible to use the light source device 3 during the processing. If the waiting time is too long, it may be a trouble for the normal operation of the light source device 3. Accordingly, the waiting time for the automatic adjustment has been set to a predetermined value in advance. If the waiting time reaches the set time, the automatic adjustment processing is stopped and in step S18, a latest adjustment data stored in storage device such as nonvolatile storage device, for example, a flash memory, is read out and the data is used as the adjustment data of the current processing. A default value of the waiting time count value T is 0, and the value is initialized at every power supply. The contents of the adjustment data is described below.

In step S6, predetermined voltage is applied to the diaphragm driving part 25 through the D/A conversion circuit 27 via the drive signal line L1. The diaphragm blade 21 is rotated by the diaphragm driving part 25, and fixed at a set opening position. The set opening position of the diaphragm blade 21 can be set at any position within a fully-opened position and a fully-closed position.

The processing proceeds to step S7, and differences in the braking coil system that brakes the rotation operation of the diaphragm blade 21 is adjusted. Then, the processing proceeds to step S8, and the CPU 26 checks whether the difference adjustment of the braking coil system has been completed or not. If the difference adjustment has not been completed, the processing proceeds to step S9, the elapsed time count value T is incremented (T←T+1), and the processing returns to step S5. If the difference adjustment of the braking coli system has been completed, the processing proceeds to step S10.

As described above, the induced electromotive force is generated in the braking coil as the diaphragm blade 21 rotates, and accordingly, the induced electromotive force is not generated in a state in which the diaphragm blade 21 is fixed at a certain position. However, due to the variations in the braking coil or the amplifier, voltage amplified by the amplifier may be outputted. In step S7, certain voltage is applied to the adjustment circuit 28 via the D/A conversion circuit 30, and the processing is repeated until the voltage outputted from the adjustment circuit 28 becomes 0 [V] within the range $T<T_0$.

Then, the processing proceeds to step S10, and in steps S10 to S14, processing to adjust the error generated between the voltage width detected by the potentiometer and the maximum rotation range of the diaphragm blade 21 is performed.

First, in step S10, the diaphragm blade 21 is rotated to the fully-opened position that has been set as the predetermined position in advance. Whether the diaphragm blade 21 is fully-opened or not is determined using the value outputted from the potentiometer. That is, the maximum voltage (1024 in 10-bit expression) is applied to the diaphragm driving part 25 from the CPU 26 side so that the arm 21a of the diaphragm blade 21 is latched by the stopper pin 24b.

Then, in step S11, the voltage to be applied to the diaphragm driving part 25 is gradually reduced from the maximum voltage and the change of the voltage data during the processing is acquired. At the time right after the voltage applied to the diaphragm driving part 25 is reduced from the maximum voltage, the arm 21a of the diaphragm blade 21 has still been latched by the stopper pin 24b. Accordingly, the voltage outputted from the potentiometer is constant. Then, if the maximum voltage is further reduced, the arm 21*a* of the diaphragm blade 21 starts to separate from the stopper pin 24*b* at a certain voltage. In response to the movement, since the voltage outputted from the potentiometer changes, the voltage (in FIGS. 3, A', B', C', and D' of each characteristic) detected by the potentiometer at the time right before the change is acquired as fully-opened voltage data that shows control range limit values of the fully-opened side. The fully-opened voltage data corresponds to fixed position information.

Then, the processing proceeds to step S12, and the CPU 26 checks whether the fully-opened voltage data of the diaphragm drive instruction voltage is acquired or not. If it is determined that the fully-opened voltage data is not acquired, the processing returns to step S9. If the fully-opened voltage data of the diaphragm drive instruction voltage is acquired, the processing proceeds to step S13.

In step S13, at the diaphragm drive instruction voltage of 0 [V], the diaphragm blade 21 is operated to the fully-closed position that has been set as the predetermined position in advance. Then, in step S14, the voltage to be applied to the diaphragm driving part 25 is gradually increased, and the change of the voltage data during the processing is acquired. At the time right after the voltage applied to the diaphragm driving part 25 is increased from the voltage of 0 [V], the arm 21*a* of the diaphragm blade 21 has still been latched by the stopper pin 24*b*. Accordingly, the voltage outputted from the potentiometer is constant. Then, if the diaphragm drive instruction voltage is further increased, the arm 21*a* of the diaphragm blade 21 starts to separate from the stopper pin 24*b* at a certain voltage. In response to the movement, since the voltage outputted from the potentiometer changes, the voltage (in FIGS. 3, A, B, C, and D of each characteristic) detected at the time right before the change is acquired as fully-closed voltage data that is control range limit values of the fully-closed side. The fully-closed voltage data corresponds to the fixed position information.

Then, the processing proceeds to step S15, and the CPU 26 checks whether the fully-closed voltage data of the diaphragm drive instruction voltage is acquired or not. If it is determined that the fully-closed voltage data is not acquired, the processing returns to step S9. If the fully-closed voltage data of the diaphragm drive instruction voltage is acquired, the processing proceeds to step S16.

In step S16, based on the acquired fully-opened voltage data and the fully-closed voltage data, adjustment data of adjustment of the characteristics between the voltage widths detected by the potentiometer and the maximum rotation range of the diaphragm blade 21 is generated. The adjustment data can be expressed, for example, by a linear expression with a certain slope linearly connecting two points of the fully-opened voltage data and the fully-closed voltage data. Alternatively, the adjustment data may be formed by data stored as table data of a relationship between the diaphragm voltages and the openings of the diaphragm blade 21 calculated according to the linear expression. The processing performed in step S16 corresponds to the control range setting part for regulating the control range of the opening/closing amounts of the diaphragm blade 21.

Then, the processing proceeds to step S17. In step S17, the previous adjustment data stored as backup data in the storage device such as the nonvolatile storage device, represented by, the flash memory, is updated (overwritten) by the adjustment data generated in the processing of this time, and the processing returns to step S4. Accordingly, the adjustment data generated in this time becomes a latest data stored in the storage device.

After the processing returned to step S4, as described above, whether the automatic adjustment is competed or not is checked, and if the automatic adjustment is competed, the processing proceeds to step S19.

On the other hand, if the processing proceeds from step S2 or S5 to step S18, the latest data (since the generation of the adjustment data of this time has been failed, the previously generated adjustment data) stored in the storage device is acquired, and the processing proceeds to step S19.

In step S19, the CPU 26 takes in the adjustment data of this time generated in step S16 or the latest adjustment data acquired in step S18, and executes a normal operation mode for performing luminance adjustment of the light source device 3. When the operation of the light source device 3 is completed, that is, the power switch is turned off, the routine is finished.

As described above, according to the present embodiment, in response to the power supply to the light source device 3, an error generated between a voltage width detected by the potentiometer and a maximum rotation range of the diaphragm blade 21 is automatically adjusted. Accordingly, manual adjustment operation is not required in the production process, and the production man-hour can be reduced. Moreover, even after the diaphragm unit 22 has been mounted in the light source device 3, the adjustment can be performed. Accordingly, if an error is generated due to foreign elements such as vibration in transportation after the assembly, the error can be appropriately adjusted. Further, an error generated across the ages can also be readily adjusted. As a result, high adjustment accuracy can be achieved and the maintenance costs can be reduced.

Now, the normal operation mode for luminance adjustment performed in step S19 is described. The diaphragm control circuit part 23 compares a light adjustment signal that is outputted from the CCU 4 and corresponds to brightness of the current image with unique luminance that is set in advance. According to the difference, a target opening Im of the diaphragm blade 21 is set. Then, based on the target opening Im, the diaphragm control circuit part 23 sets diaphragm drive instruction voltage according to the relationship between the voltage width that has been detected by the potentiometer in advance and the maximum rotation range of the diaphragm blade 21 using a linear expression set for each diaphragm unit 22, or referring to table data obtained according to the linear expression.

As shown in FIG. 3, if differences exist between the voltage widths detected by the potentiometer and the maximum rotation range of the diaphragm blade 21, with respect to the target opening Im of the diaphragm blade 21, the diaphragm drive instruction voltages of each characteristic differ from each other. In the present embodiment, for the diaphragm unit 22 mounted in the light source device 3, a characteristic between the voltage width detected by the potentiometer and the maximum rotation range of the diaphragm blade 21 is set, and according to the set characteristic, the diaphragm drive instruction voltage corresponding to the target opening Im is set. Accordingly, stable luminance can be obtained and high reliability can be obtained.

The diaphragm drive instruction voltage is outputted to the diaphragm driving part 25 of the diaphragm unit 22, and the diaphragm blade 21 is rotated to the target opening Im. The opening of the diaphragm blade 21 is detected by the potentiometer. The CPU 26 reads an actual opening of the diaphragm blade 21 detected by the potentiometer and feedback-controls the diaphragm blade 21 so that the actual opening is to be contracted to the target opening Im. In the present embodiment, an error generated between a voltage width detected by the potentiometer and a maximum rotation range of the diaphragm blade 21 is automatically adjusted. Accordingly, the actual opening of the diaphragm blade 21 to the target opening Im is not largely displaced, and the feedback control amount is small. Accordingly, good response can be obtained.

It is to be understood that the present invention is not limited to the above-described embodiment. For example, the diaphragm driving part 25 may be controlled using not only the voltage control, but also the diaphragm blade 21 may be opened or closed using a current control.

Having described the preferred embodiment of the invention referring to the accompanying drawings, it should be understood that the present invention is not limited to the precise embodiment and various changes and modifications thereof could be made by one skilled in the art without departing from the spirit or scope of the invention as defined in the appended claims.

What is claimed is:

1. A light source device comprising:
   a light source;
   a diaphragm member for adjusting light quantity of illumination light supplied from the light source; and
   a diaphragm driving part for driving the diaphragm member to perform opening operation or closing operation;
   an opening/closing control part for setting electric energy to be supplied to the diaphragm driving part and controlling an opening/closing amount of the diaphragm member;
   a control range setting part for detecting fixed position information at a time the diaphragm member is fixed at a predetermined position, setting adjustment data for adjusting a drive signal outputted from the opening/closing control part and opening/closing positions of the diaphragm member based on the fixed position information, and regulating a control range of the opening/closing control part based on the adjustment data, wherein the predetermined position can be one of a fully-opened position and a fully-closed position of the diaphragm member; and
   a stopper member fixed to a base to which the diaphragm driving part is fixed and configured to restrict a rotation range of the diaphragm member is provided at the fully-opened position and the fully-closed position,
   wherein a voltage control range of the diaphragm driving part is set to be wider than a maximum rotation range of the diaphragm member restricted by the stopper member, and
   wherein the control range setting part causes the diaphragm member to be moved with an electric energy that can move the diaphragm member beyond a rotation range restricted by the stopper member on the fully-opened position, and stopped by the stopper member at the fully-opened position, detects the fixed position information on the fully-opened position based on position detection information showing the position of the diaphragm member when the diaphragm member is stopped by the stopper member, and sets the fixed position information as control range limit values of the fully-opened position of the opening/closing control part, or, the control range setting part causes the diaphragm member to be moved with an electric energy that can move the diaphragm member beyond a rotation range restricted by the stopper member on the fully-closed position, and stopped by the stopper member at the fully-closed position, detects the fixed position information on the fully-closed position based on position detection information showing the position of the diaphragm member when the diaphragm member is stopped by the stopper member, and sets the fixed position information as control range limit values of the fully-closed position of the opening/closing control part.

2. The light source device according to claim 1, further comprising:
   an adjustment instruction device for instructing adjustment start,
   wherein the control range setting part detects an instruction signal from the adjustment instruction device and starts the adjustment of the drive signal outputted from the opening/closing control part and the opening/closing positions of the diaphragm member.

3. The light source device according to claim 1, wherein the control range setting part detects a signal for turning on a power supply and starts the adjustment of the drive signal outputted from the opening/closing control part and the opening/closing positions of the diaphragm member.

4. The light source device according to claim 1, wherein the control range setting part starts the adjustment of the drive signal outputted from the opening/closing control part and the opening/closing positions of the diaphragm member if the number of times of power supply reaches a set number of times or total operating time reaches a set time.

5. The light source device according to claim 1, further comprising:
   a storage device for storing the adjustment data set in the control range setting part.

6. The light source device according to claim 5, wherein a control range setting part sets the control range limit value based on a latest adjustment data stored in the storage device if the fixed position information is not detected even if the set time has passed.

7. The light source device according to claim 1, further comprising:
   a braking coil for generating induced electromotive force using operation of the diaphragm member; and
   an adjustment circuit for adjusting the induced electromotive force,
   wherein the control range setting part performs adjustment so that an output value outputted from the adjustment circuit at the time the diaphragm member is fixed at the predetermined position is to be a constant value.

8. An endoscope device comprising:
   the light source device according to claim 1; and
   an endoscope that irradiates the illumination light supplied from the light source device to a subject and takes in light reflected from the subject.

* * * * *